United States Patent
Abe et al.

(10) Patent No.: US 9,290,525 B2
(45) Date of Patent: Mar. 22, 2016

(54) METHOD FOR PRODUCING CYCLIC SILANE COMPOUND OR SALT THEREOF, SALT HAVING CYCLIC SILANE DIANION, AND CYCLIC SILANE DIANION SALT-CONTAINING COMPOSITION

(71) Applicant: Nippon Shokubai Co., Ltd., Osaka (JP)

(72) Inventors: Takashi Abe, Osaka (JP); Shin-ya Imoto, Hyogo (JP); Morihiro Kitamura, Osaka (JP); Hikaru Takahashi, Osaka (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 69 days.

(21) Appl. No.: 13/934,577

(22) Filed: Jul. 3, 2013

(65) Prior Publication Data

US 2014/0012030 A1    Jan. 9, 2014

(30) Foreign Application Priority Data

Jul. 4, 2012    (JP) ................................. 2012-150920

(51) Int. Cl.
    C07F 7/04        (2006.01)
    C07F 9/54        (2006.01)
    C07C 211/63     (2006.01)
    C07C 209/68     (2006.01)

(52) U.S. Cl.
    CPC ............. *C07F 9/5442* (2013.01); *C07C 209/68* (2013.01); *C07C 211/63* (2013.01)

(58) Field of Classification Search
    CPC ........................... C07F 9/5442; C07C 209/68
    USPC ........................................................ 556/430
    See application file for complete search history.

(56) References Cited

U.S. PATENT DOCUMENTS

| | | | |
|---|---|---|---|
| 5,942,637 | A | 8/1999 | Boudjouk et al. |
| 2001/0021760 | A1 | 9/2001 | Matsuki et al. |
| 2002/0076378 | A1 | 6/2002 | Wolfe et al. |
| 2012/0294791 | A1 | 11/2012 | Elangovan et al. |

FOREIGN PATENT DOCUMENTS

| | | |
|---|---|---|
| JP | S54-24874 | 2/1979 |
| JP | S54-130541 | 10/1979 |
| JP | 2001-253706 | 9/2001 |
| JP | 4519955 | 5/2010 |
| WO | 2011/094191 | 8/2011 |
| WO | WO 2011094191 A1 * | 8/2011 |

OTHER PUBLICATIONS

E. Hengge and H. Firgo, J Organometallic Chemistry, 212 (1981) 155-161.*
Shimoda et al., "Solution-processed silicon films and transistors", Nature, vol. 440, Apr. 6, 2006, pp. 783-786.
Office Action issued Aug. 11, 2015 in corresponding Japanese Application No. 2012-150920, with English translation.
Office Action issued Sep. 15, 2015 in corresponding Japanese Application No. 2012-150907, with English translation.
Hengge et al., "An electrochemical method for the synthesis of silicon—silicon bonds", Journal of Organometallic Chemistry, vol. 212, 1981, pp. 155-161.

* cited by examiner

*Primary Examiner* — Porfirio Nazario Gonzalez
*Assistant Examiner* — Kofi Adzamli
(74) *Attorney, Agent, or Firm* — Wenderoth, Lind & Ponack, L.L.P.

(57) ABSTRACT

An object of the present invention is to provide a production method that can efficiently produce a cyclic silane compound or a salt thereof with a high yield and to provide a novel salt having a cyclic silane dianion that is easy to handle and a cyclic silane dianion salt-containing composition. The method for producing a cyclic silane compound or a salt thereof of the present invention includes the step of allowing a halosilane compound to react in the presence of at least one of a phosphonium salt and an ammonium salt, and a compound represented by a specific formula.

10 Claims, No Drawings

METHOD FOR PRODUCING CYCLIC SILANE COMPOUND OR SALT THEREOF, SALT HAVING CYCLIC SILANE DIANION, AND CYCLIC SILANE DIANION SALT-CONTAINING COMPOSITION

BACKGROUND OF THE INVENTION (1) Field of the Invention

The present invention relates to a production method that can efficiently obtain a cyclic silane compound or a salt thereof by a simple method, a novel salt having a cyclic silane dianion, and a cyclic silane dianion salt-containing composition.

(2) Description of Related Art

A silane compound is widely utilized as a raw material of silicon and silica, and a water-reactive combustible gas such as monosilane and disilane is mostly used. On the other hand, a route of synthesizing a middle molecular weight silicon compound is not sufficiently known, due to its unique reactivity. Particularly, a six-membered cyclic silicon compound and a salt of the compound are liquid or solid, are relatively stable, and, therefore, utility thereof is expected, but a synthesis method is limited and is not sufficiently utilized.

Among its limited reported examples, there is a salt of tetradecachlorocyclohexasilane dianion that is a six-membered cyclic silicon compound (Japanese Patent No. 4519955 and WO 2011/094191). Japanese Patent No. 4519955 suggests a method for synthesizing a salt of tetradecachlorocyclohexasilane dianion using a tertiary polyamine such as N,N,N',N'',N''-pentaethyldiethylenetriamine (pedeta) or N,N,N',N'-tetraethylethylenediamine (teeda). WO 2011/094191 suggests that tetradecachlorocyclohexasilane dianion can be produced with a high yield by using a specific amine, in addition to pedeta and teeda described above.

SUMMARY OF THE INVENTION

In view of the above, an object of the present invention is to provide a production method that can efficiently produce a cyclic silane compound or a salt thereof with a high yield and to provide a novel salt having a cyclic silane dianion that is easy to handle and a cyclic silane cyclic dianion salt-containing composition.

As a result of the extensive studies to solve the above problems, the present inventors have found that, when a cyclic silane compound such as tetradecahalocyclohexasilane dianion or a salt thereof is synthesized from a halosilane compound, a phosphonium salt or an ammonium salt and a chelating ligand having a specific structure (chelate forming agent) are concurrently used, in place of the conventional tertiary polyamine, whereby a cyclic silane compound or a salt thereof (novel cyclic silane dianion salt) can be efficiently obtained, and the cyclic silane compound or the salt thereof thus obtained contains no silicon atom in a cation and thus silane is not generated even if the cation is decomposed, and the cyclic silane dianion salt has not only a silicon-halogen bond but also a silicon-hydrogen bond, and thus many reactants can be selected and used, and handling thereof can be facilitated. Based on these findings, the present invention has been accomplished.

That is, a method for producing a cyclic silane compound or a salt thereof of the present invention comprises the step of allowing a halosilane compound to react in the presence of at least one of a phosphonium salt and an ammonium salt, and a compound represented by the following general formula (i).

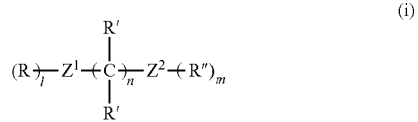

wherein $Z^1$ represents N, O, P or S; $Z^2$ represents O, P or S; R and R'' each independently represent an organic group having a carbon number of 1 to 20, which may contain O, P, S or a halogen atom and may have a straight-chain structure, a branched structure, an alicyclic structure or an aromatic ring structure; R' represents a hydrogen atom, or an organic group having a carbon number of 1 to 6, which may have a straight-chain structure, a branched structure or a ring structure; l is 2 when $Z^1$ is N or P, l is 1 when $Z^1$ is O or S, m is 2 when $Z^2$ is P, and m is 1 when $Z^2$ is O or S; n is an integer of 1 to 5; and when R, R' or R'' is each plurally present, each may be the same or different.

The above reaction is preferably carried out in the presence of a basic compound. In addition, the phosphonium salt or the ammonium salt is preferably a quaternary phosphonium salt or a quaternary ammonium salt, respectively. Furthermore, the phosphonium salt is preferably a salt represented by the following general formula (ii), and the ammonium salt is preferably a salt represented by the following general formula (iii).

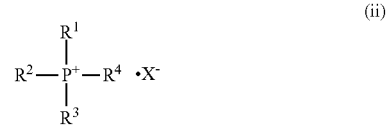

wherein $R^1$ to $R^4$ each independently represent a hydrogen atom, an alkyl group or an aryl group; and $X^-$ represents a monovalent anion.

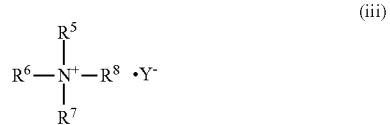

wherein $R^5$ to $R^8$ each independently represent a hydrogen atom, an alkyl group or an aryl group; and $Y^-$ represents a monovalent anion.

In addition, the present invention encompasses a salt having a cyclic silane dianion represented by the following general formula (vi).

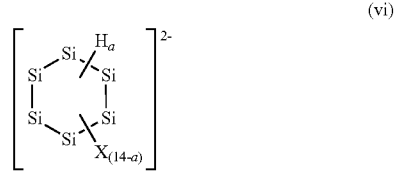

wherein X represents a halogen element; and a represents an integer of 1 to 6.

Furthermore, the present invention encompasses a cyclic silane dianion salt-containing composition containing the salt having a cyclic silane dianion represented by the general formula (vi) and a salt having a cyclic silane dianion represented by the following general formula (vii). In this cyclic silane dianion salt-containing composition, the salt having a cyclic silane dianion represented by the following general formula (vii) is preferably contained in an amount of 1 to 10000 parts by mass, based on the total amount of 100 parts by mass of the salt having a cyclic silane dianion represented by the general formula (vi).

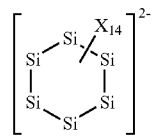

(vii)

wherein X represents a halogen element.

According to the method for producing a cyclic silane compound or a salt thereof of the present invention, the production is carried out using an easily available phosphonium salt or ammonium salt and a halosilane compound as raw materials, in the presence of a compound having a specific structure represented by the general formula (i) (i.e., chelating ligand), thus one containing no silicon atom other than the silicon atom forming a ring structure, for example, one containing no silicon atom in a counter cation, is produced, whereby a versatile inexpensive production is possible. Furthermore, the salt having a cyclic silane dianion of the present invention has both a silicon-halogen bond and a silicon-hydrogen bond in the structure, and thus many reactants can be selected, whereby introduction of a silane structure into a variety of compounds is consequently possible.

DETAILED DESCRIPTION OF THE PREFERRED EMBODIMENTS

Method for Producing Cyclic Silane Compound or Salt Thereof

The method for producing a cyclic silane compound or a salt thereof of the present invention includes the step of allowing a halosilane compound to react in the presence of at least one of a phosphonium salt and an ammonium salt, and a chelating ligand represented by the following general formula (i). In this step, the halosilane compound is cyclically coupled, to be formed into a halogenated cyclic silane compound or a salt thereof. The obtained salt may contain a cyclic silane dianion.

Examples of the halosilane compound for use as a raw material include trihalogenated silanes such as trichlorosilane, tribromosilane, triiodosilane and trifluorosilane; dihalogenated silanes such as dichlorosilane, dibromosilane, diiodosilane and difluorosilane; and tetrahalogenated silanes such as tetrachlorosilane, tetrabromosilane, tetraiodosilane and tetrafluorosilane; and among them, trihalogenated silanes are preferable, and trichlorosilane is particularly preferable.

The compound represented by the following general formula (i) is presumed to contribute to a cyclic coupling reaction of the halosilane compound as a chelating ligand; thus a cyclic silane compound or a salt thereof can be produced with a good reactivity by carrying out the reaction in the presence of the compound represented by the general formula (i).

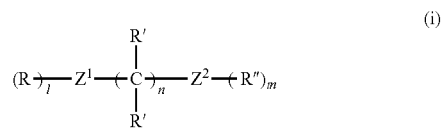

(i)

wherein $Z^1$ represents N, O, P or S; $Z^2$ represents O, P or S; R and R" each independently represent an organic group having a carbon number of 1 to 20, which may contain O, P, S or a halogen atom and may have a straight-chain structure, a branched structure, an alicyclic structure or an aromatic ring structure; R' represents a hydrogen atom, or an organic group having a carbon number of 1 to 6, which may have a straight-chain structure, a branched structure or a ring structure; l is 2 when $Z^1$ is N or P, l is 1 when $Z^1$ is O or S, m is 2 when $Z^2$ is P, and m is 1 when $Z^2$ is O or S; n is an integer of 1 to 5; and when R, R' or R" is each plurally present, each may be the same or different.

In the general formula (i), while $Z^1$ represents N, O, P or S and $Z^2$ represents O, P or S, $Z^1$ preferably represents O or P and $Z^2$ preferably represents O or P. More preferably, $Z^1$ and $Z^2$ are the same element.

In the general formula (i), n may be an integer of 1 to 5, and is preferably not more than 4, more preferably not more than 3, and further preferably not more than 2.

In the general formula (i), R' is a hydrogen atom or an organic group having a carbon number of 1 to 6 (hydrocarbon group or the like), and particularly, R' is preferably a hydrogen atom or an alkyl group having a carbon number of 1 to 6, and more preferably a hydrogen atom. Particularly, among R's that are plurally (2 n) present, the hydrogen atom number is preferably not less than 0.5 n, more preferably not less than n, and further preferably not less than 1.5 n. When R' is an organic group, the carbon number is preferably a carbon number of 1 to 5, more preferably a carbon number of 1 to 4, and further preferably a carbon number of 1 to 3. Here, individual R' or two R's bound to the same carbon atom may be the same or different, and a plurality of R's, particularly two R's bound to the same carbon atom, are desirably the same.

The organic group represented by R' in the general formula (i) may have a straight-chain structure, a branched structure or a ring structure, and further, two R's among 2 n of R's may be directly bound to form a ring. As an example of the case where two R's are directly bound to form a ring, dialkoxycyclohexanes such as 1,1-dimethoxycyclohexane are included.

In the general formula (i), specific examples of the organic group represented by R' include alkyl groups such as a methyl group, an ethyl group, a n-propyl group, an i-propyl group, a n-butyl group, a s-butyl group, a t-butyl group, a pentyl group and a hexyl group as those having a straight-chain structure or a branched structure, and a cyclohexyl group as those having a ring structure.

In the general formula (i), R and R" are each independently an organic group having a carbon number of 1 to 20, preferably 1 to 15, and more preferably 1 to 10, which may contain O, P, S or a halogen atom (preferably Cl, Br, I or the like), and R and R" may be different but preferably be the same. Furthermore, when R or R" is each plurally present, they are each desirably the same. The organic group represented by R or R" in the general formula (i) may have a straight-chain structure, a branched structure, an alicyclic structure or an aromatic ring structure, and further, one R and one R" may be directly bound to form a ring. As an example of the case where one R and one R" may be directly bound to form a ring, dioxane, substituted dioxane such as 4-methyl-1,3-dioxane, dioxolane, and the like are included.

In the general formula (i), specific examples of the organic group represented by R and R" include alkyl groups such as a methyl group, an ethyl group, a n-propyl group, an i-propyl group, a n-butyl group, a s-butyl group, a t-butyl group, a pentyl group, a hexyl group, an octyl group, a 2-ethylhexyl group, a decyl group, and a dodecyl group as those having a straight-chain structure or a branched structure, a cyclohexyl group, an adamantyl group, and the like, as those having an alicyclic structure, and aryl groups such as phenyl, benzyl, 1-naphthyl, and 2-naphthyl as those having an aromatic structure.

The compound represented by the general formula (i) (chelating ligand) is particularly preferably a compound containing two or more O or P in order to express good chelating ability. Preferable specific examples of the chelating ligand include, as the compound containing two O, dialkoxyalkanes such as 1,1-dimethoxyethane, 1,2-dimethoxyethane, 1,2-diethoxyethane, 1,2-dipropoxyethane, 1,2-diisopropoxyethane, 1,2-dibutoxyethane, 1,2-diphenoxyethane, 1,3-dimethoxypropane, 1,3-diethoxypropane, 1,3-dipropoxypropane, 1,3-diisopropoxypropane, 1,3-dibutoxypropane, 1,3-diphenoxypropane, 1,4-dimethoxybutane, 1,4-diethoxybutane, 1,4-dipropoxybutane, 1,4-diisopropoxybutane, 1,4-dibutoxybutane and 1,4-diphenoxybutane, and particularly preferably include 1,2-dimethoxyethane.

In addition, preferable specific examples of the chelating ligand include, as the compound containing two P, bis(dialkylphosphino)alkanes and bis(diarylphosphino)alkanes such as 1,2-bis(dimethylphosphino)ethane, 1,2-bis(diethylphosphino)ethane, 1,2-bis(dipropylphosphino)ethane, 1,2-bis(dibutylphosphino)ethane, 1,2-bis(diphenylphosphino)ethane, 1,3-bis(dimethylphosphino)propane, 1,3-bis(diethylphosphino)propane, 1,3-bis(dipropylphosphino)propane, 1,3-bis(dibutylphosphino)propane, 1,3-bis(diphenylphosphino)propane, 1,4-bis(dimethylphosphino)butane, 1,4-bis(diethylphosphino)butane, 1,4-bis(dipropylphosphino)butane, 1,4-bis(dibutylphosphino)butane and 1,4-bis(diphenylphosphino)butane, and particularly preferably include 1,2-bis(diphenylphosphino)ethane. Here, the compound represented by the general formula (i) (chelating ligand) may be used alone or in combination of two or more thereof.

The amount (total amount) of the compound represented by the general formula (i) (chelating ligand) to be used is preferably not less than 0.01 mol and not more than 50 mol, more preferably not less than 0.05 mol and not more than 40 mol, and further preferably not less than 0.1 mol and not more than 30 mol, based on 1 mol of the halosilane compound. When the amount of the chelating ligand is too small, the halosilane compound is unreacted, and the yield of the cyclic silane compound or the salt thereof may be lowered. On the other hand, when the amount of the chelating ligand is too large, the purity of the cyclic silane compound or the salt thereof may be lowered.

The phosphonium salt is preferably a quaternary phosphonium salt, and preferably includes a salt represented by the following general formula (ii).

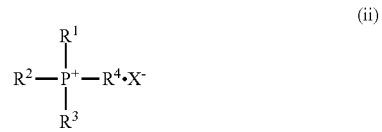

(ii)

wherein $R^1$ to $R^4$ each independently represent a hydrogen atom, an alkyl group or an aryl group; and $X^-$ represents a monovalent anion.

In the general formula (ii), the alkyl groups as examples of $R^1$ to $R^4$ preferably include alkyl groups having a carbon number of 1 to 16 such as a methyl group, an ethyl group, a propyl group, a butyl group, a pentyl group, a hexyl group, a heptyl group, an octyl group and a cyclohexyl group, and the aryl groups as examples of $R^1$ to $R^4$ preferably include aryl groups having a carbon number of 6 to 18 such as a phenyl group and a naphthyl group. Among them, a butyl group (Bu) and a phenyl group (Ph) are particularly preferable as $R^1$ to $R^4$. In addition, $R^1$ to $R^4$ may be each different, but all are preferably the same group.

In the general formula (ii), the monovalent anion represented by $X^-$ includes halide ions ($Cl^-$, $Br^-$, $I^-$, and the like), borate ions ($BF_4^-$ and the like), and phosphorous anions ($PF_6^-$ and the like). Among them, $Cl^-$, $Br^-$ and $I^-$ are preferable, and $Cl^-$ and $Br^-$ are particularly preferable, from the viewpoint of easy availability. Here, the phosphonium salt may be used alone or in combination of two or more thereof.

The ammonium salt is preferably a quaternary ammonium salt, and preferably includes a salt represented by the following general formula (iii).

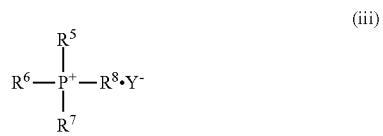

(iii)

wherein $R^5$ to $R^8$ each independently represent a hydrogen atom, an alkyl group or an aryl group; and $Y^-$ represents a monovalent anion.

In the general formula (iii), the alkyl groups as examples of $R^5$ to $R^8$ preferably include alkyl groups having a carbon number of 1 to 16 such as a methyl group, an ethyl group, a propyl group, a butyl group, a pentyl group, a hexyl group, a heptyl group, an octyl group and a cyclohexyl group, and the aryl groups as examples of $R^5$ to $R^8$ preferably include aryl groups having a carbon number of 6 to 18 such as a phenyl group and a naphthyl group. Among them, a butyl group (Bu) and a phenyl group (Ph) are particularly preferable as $R^5$ to $R^8$. In addition, $R^5$ to $R^8$ may be each different, but all are preferably the same group.

In the general formula (iii), the monovalent anion represented by $Y^-$ includes halide ions ($Cl^-$, $Br^-$, $I^-$, and the like), borate ions ($BF_4^-$ and the like), and phosphorous anions ($PF_6^-$ and the like). Among them, $Cl^-$, $Br^-$ and $I^-$ are preferable, and $Cl^-$ and $Br^-$ are particularly preferable, from the viewpoint of easy availability. Here, the ammonium salt may be used alone or in combination of two or more thereof.

The amount (total amount) of the phosphonium salt or the ammonium salt to be used is preferably not less than 0.01 mol and not more than 0.5 mol, more preferably not less than 0.05 mol and not more than 0.4 mol, and further preferably not less than 0.08 mol and not more than 0.3 mol, based on 1 mol of the halosilane compound. When the amount of the phosphonium salt or the ammonium salt is too small, the halosilane compound is unreacted, and the yield of the cyclic silane compound or the salt thereof may be lowered. On the other hand, when the amount of the phosphonium salt or the ammonium salt is too large, the purity of the cyclic silane compound or the salt thereof may be lowered.

In the production method of the present invention, the reaction is preferably carried out in the presence of a basic compound. Examples of the basic compound include amine compounds, and preferably include monoamine compounds among them. Specific examples preferably include triethylamine, tripropylamine, tributylamine, trioctylamine, triisobutylamine, triisopentylamine, diethylmethylamine, diisopropylethylamine, dimethylbutylamine, dimethyl-2-ethylhexylamine, diisopropyl-2-ethylhexylamine, and methyldioctylamine. Among them, diisopropylethylamine is particularly preferable. Here, the basic compound may be used alone or in combination of two or more thereof.

The amount (total amount) of the basic compound to be used may be properly set depending on the type or the like. For example, in the case of a monoamine compound, the amount is preferably not less than 0.10 mol and not more than 2 mol, more preferably not less than 0.20 mol and not more than 1.8 mol, and further preferably not less than 0.40 mol and not more than 1.5 mol, based on 1 mol of the halosilane compound. When the amount of the basic compound (monoamine compound) is too small, the halosilane compound is unreacted, and the yield of the cyclic silane compound or the salt thereof may be lowered. On the other hand, when the amount of the basic compound (monoamine compound) is too large, lowering of the yield and purity of the cyclic silane compound or the salt thereof may be caused.

The production method of the present invention can be carried out in an organic solvent as necessary. This organic solvent is preferably a solvent that does not prevent a cyclic coupling reaction, and examples preferably include halogenated hydrocarbon solvents (for example, chloroform, dichloromethane and 1,2-dichloroethane), ether solvents (for example, diethyl ether, tetrahydrofuran, cyclopentyl methyl ether, diisopropyl ether and methyl tertiary butyl ether), and aprotic polar solvents such as acetonitrile, N,N-dimethylformamide and dimethylsulfoxide. Among them, chlorinated hydrocarbon solvents such as chloroform, dichloromethane and 1,2-dichloroethane are preferable, and 1,2-dichloroethane is particularly preferable. Here, these organic solvents may be used alone or in combination of two or more thereof.

The amount (total amount) of the organic solvent to be used is not particularly limited, and usually, the concentration of the halosilane compound is preferably adjusted to not less than 0.5 mol/L and not more than 10 mol/L, the concentration is more preferably not less than 0.8 mol/L and not more than 8 mol/L, and the concentration is further preferably not less than 1 mol/L and not more than 5 mol/L.

The reaction temperature in the production method of the present invention can be properly set depending on the reactivity, and is, for example, about 0° C. to 120° C., and preferably about 15° C. to 70° C. In addition, the coupling reaction is desirably carried out under substantially anhydrous conditions, and is recommended to be carried out, for example, under a dry gas (particularly, inert gas) atmosphere. The reaction time in the production method of the present invention can be properly set depending on the reaction temperature, raw materials to be used, and the like, and is, for example, preferably not less than 1 hour, more preferably not less than 2 hours, and further preferably not less than 3 hours, and preferably not more than 48 hours, and more preferably not more than about 24 hours. Furthermore, during the reaction, stirring may be carried out simultaneously with heating in order to accelerate the reaction. The cyclic silane compound or the salt thereof generated in the production method of the present invention can be easily isolated from the reaction solution by filtration or the like.

The cyclic silane compound or the salt thereof obtained by the production method of the present invention is a compound or salt containing a ring formed by continuous six silicon atoms of the halosilane compound, and contains no silicon atom other than the silicon atom forming this ring structure; thus it is, for example, one containing no silicon atom in a counter cation. The above ring may be ionized with a plurality of halogens to form a salt with a counter ion, and may be a compound neutralized with a plurality of halogens. For example, when trichlorosilane is used as the halosilane compound, a six-membered ring consisting of six silicon atoms is formed as a dianion, to obtain a salt having a cation that forms an onium salt as a counter ion. Specifically, when trichlorosilane is used as the halosilane compound, and a compound in which, in the general formula (ii), $X^-$ is a chloride ion ($Cl^-$) and $R^1$ to $R^4$ are a phenyl group is used as the phosphonium salt, a salt of a cyclic silane dianion and a cation derived from the phosphonium salt, such as dodecachlorodihydrocyclohexasilane dianion salt ($[Ph_4P^+]_2[Si_6H_2Cl_{12}]^{2-}$), tridecachlorohydrocyclohexasilane dianion salt ($[Ph_4P^+]_2[Si_6HCl_{13}]^{2-}$), and tetradecachlorocyclohexasilane dianion salt ($[Ph_4P^+]_2[Si_6Cl_{14}]^{2-}$) as in the following general formula (iv) is a cyclic silane dianion salt. In addition, when trichlorosilane is used as the halosilane compound, and a compound in which, in the general formula (ii), $X^-$ is a bromide ion ($Br^-$) and $R^1$ to $R^4$ are a phenyl group is used as the phosphonium salt, a salt of a cyclic silane dianion in which tetradecahalocyclohexasilane dianion salt ($[Si_6Y_{14}]^{2-}$; wherein Y is Cl or Br) as in the following general formula (v) and a part of chlorine atoms is substituted with hydrogen, and a cation derived from the phosphonium salt, is a cyclic silane dianion salt.

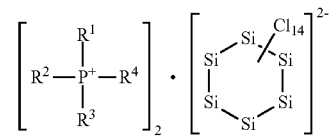

(iv)

wherein $R^1$ to $R^4$ each independently represent a hydrogen atom, an alkyl group or an aryl group; and an alkyl group and an aryl group are the same as in the formula (ii).

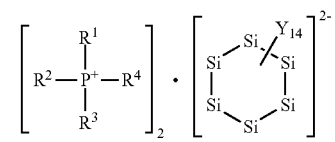

(v)

wherein $R^1$ to $R^4$ each independently represent a hydrogen atom, an alkyl group or an aryl group; an alkyl group and an aryl group are the same as in the formula (ii); and Y represents Cl, Br, or a hydrogen atom.

(Salt of Cyclic Silane Compound/Cyclic Silane Dianion Salt)

Next, the salt having a cyclic silane dianion of the present invention will be further specifically described. The salt having a cyclic silane dianion of the present invention has a cyclic silane dianion represented by the following general formula (vi).

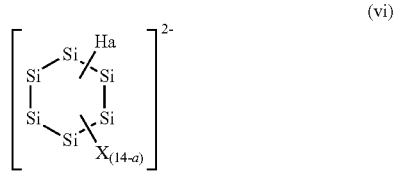

(vi)

wherein X represents a halogen element; and a represents an integer of 1 to 6.

X in the general formula (vi) represents a halogen element, and is preferably Cl, Br, or I, more preferably, Cl or Br, and further preferably Cl. When X is Cl, a raw material is easily available, and inexpensive production is possible. a represents an integer of 1 to 6, preferably 1 to 4, more preferably 1 to 3, and further preferably 1 or 2.

The counter cation is not limited, and for example, a cation derived from the phosphonium salt represented by the general formula (ii) and a cation derived from the ammonium salt represented by the general formula (iii) are preferably adopted.

The salt having a cyclic silane dianion of the present invention can be produced by the above production method, and the preferable range of the raw materials and production conditions are also the same. Here, a solvent, or the compound represented by the general formula (i) that is presumed to contribute as a chelating ligand is properly selected, whereby a in the general formula (vi), i.e., the hydrogen atom number and the compositional ratio in the cyclic silane dianion can be adjusted. The compositional ratio herein refers to the ratio of a plurality of the cyclic silane dianions that are different in the hydrogen atom number. That is, in the present invention, one or two or more salts having the cyclic silane dianion may be simultaneously produced.

The salt having the cyclic silane dianion of the present invention has both a silicon-halogen bond and a silicon-hydrogen bond in the structure, thus many reactants can be selected, and introduction of a silane structure into a variety of compounds is possible.

(Cyclic Silane Dianion Salt-Containing Composition)

The present invention also includes a cyclic silane dianion salt-containing composition containing the salt having a cyclic silane dianion represented by the general formula (vi) and a salt having a cyclic silane dianion represented by the following general formula (vii).

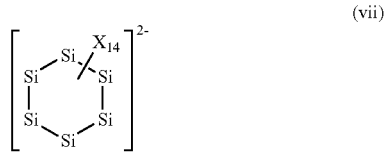

(vii)

wherein X represents a halogen element.

X in the general formula (vii) represents a halogen element, and is preferably Cl, Br, or I, more preferably, Cl or Br, and further preferably Cl. When X is Cl, a raw material is easily available, and inexpensive production is possible. The counter cation is not limited, and for example, a cation derived from the phosphonium salt represented by the general formula (ii) and a cation derived from the ammonium salt represented by the general formula (iii) are preferably adopted. In addition, the counter cation of the general formula (vii) is preferably the same as the counter cation of the general formula (vi).

The cyclic silane dianion salt-containing composition of the present invention can be produced by the above production method, and the preferable range of the raw materials and production conditions are also the same.

The salt having a cyclic silane dianion represented by the general formula (vii) is preferably contained in an amount of 1 to 10000 parts by mass, based on the total amount of 100 parts by mass of the salt having a cyclic silane dianion represented by the general formula (vi). The salt having a cyclic silane dianion represented by the general formula (vii) is contained in an amount of more preferably not less than 2 parts by mass, further preferably not less than 5 parts by mass, and most preferably not less than 8 parts by mass, and also, preferably not more than 5000 parts by mass, more preferably not more than 1000 parts by mass, further preferably not more than 500 parts by mass, most preferably not more than 400 parts by mass, and particularly preferably not more than 300 parts by mass. The salt having a cyclic silane dianion represented by the general formula (vii) is incorporated in the above ratio, whereby the total amount of hydrogen atoms in the composition can be adjusted, and when the silane structure is introduced to other compound, uniform composition can be obtained. Here, as the composition, the production conditions are set so that the intended composition is obtained by the above production method, and the obtained product may be used as it is, or the composition may be adjusted by adding some components.

It is possible to apply the salt and composition having a cyclic silane dianion of the present invention as a silicon raw material or a high performance silica raw material.

This application claims the benefit of priority based on Japanese Patent Application No. 2012-150920, filed on Jul. 4, 2012. The entire content of the specification of Japanese Patent Application No. 2012-150920, filed on Jul. 4, 2012, is incorporated into this application by reference.

EXAMPLES

The present invention will be more specifically described below with reference to Examples, but the present invention is not limited to the following Examples, and can be implemented with appropriate modifications within the scope conforming to the purport of what is mentioned above and below herein. All of such modifications are included in the technical scope of the present invention.

Here, all reactions in Examples were carried out under an inert gas (nitrogen or argon) atmosphere. Also, reagents and solvents used in the reaction in Examples were used after water and oxygen were removed.

In NMR measurements, deuterated dimethylformamide was used as a solvent, and tetramethylsilane was used as an internal standard for $^1$H and $^{29}$Si.

Indication of nuclear magnetic resonance (NMR) analyzer: NMR manufactured by Varian Inc., and NMR manufactured by Bruker Corporation Example 1

The inside of a 300-mL four-necked flask equipped with a thermometer, a condenser, a dropping funnel and a stirrer was replaced with nitrogen gas, and thereafter 11.9 g (0.032 mol) of tetraphenylphosphonium chloride, 2.97 g (0.033 mol) of 1,2-dimethoxyethane, 12.6 g (0.097 mol) of diisopropylethylamine and 100 mL of 1,2-dichloroethane were charged therein. Subsequently, while stirring the solution in the flask, 26.8 g (0.198 mol) of trichlorosilane was slowly added dropwise from the dropping funnel under the condition of 25° C.

After the completion of dropwise addition, the reaction was carried out by stirring the mixture for 2 hours, and then heating and stirring the mixture at 50° C. for 8 hours. After the reaction, the obtained solid was filtered and purified, to obtain a white solid containing 90% by mass of a mixture (cyclic silane dianion salt-containing composition) containing dodecachlorodihydrocyclohexasilane dianion salt ($[Ph_4P^+]_2[Si_6H_2Cl_{12}]^{2-}$), tridecachlorohydrocyclohexasilane dianion salt ($[Ph_4P^+]_2[Si_6HCl_{13}]^{2-}$), and tetradecachlorocyclohexasilane dianion salt ($[Ph_4P^+]_2[Si_6Cl_{14}]^{2-}$) in a mass ratio of 4:5:1.

$[Ph_4P^+]_2[Si_6H_2Cl_{12}]^{2-}$: $^{29}$Si-NMR d −47.3, −44.8, −20.9, −19.0, −18.0, −17.7, $^1$H-NMR (400 MHz) δ 3.96, 4.55, 7.82-7.91, $^{31}$P-NMR (162 MHz) δ 25.19

$[Ph_4P^+]_2[Si_6HCl_{13}]^{2-}$: $^{29}$Si-NMR (119 MHz, DMF-d6) δ −38.9 (SiHCl), −24.3 (SiCl$_2$), −23.2 (SiCl$_2$), −19.2 (SiCl$_2$), $^1$H-NMR (400 MHz) δ 5.12 (SiH), 7.82-7.91 (aryl), $^{31}$P-NMR (162 MHz) δ 25.19

($[Ph_4P^+]_2[Si_6Cl_{14}]^{2-}$: $^{29}$Si-NMR (119 MHz, DMF-d6) δ −22.99, $^1$H-NMR (400 MHz) δ 7.82-7.91, $^{31}$P-NMR (162 MHz) δ 25.19

Example 2

The inside of a 300-mL four-necked flask equipped with a thermometer, a condenser, a dropping funnel and a stirrer was replaced with nitrogen gas, and thereafter 6.72 g (0.017 mol) of tetraphenylphosphonium chloride, 6.39 g (0.016 mol) of 1,2-bis(diphenylphosphino)ethane, 6.70 g (0.052 mol) of diisopropylethylamine and 100 mL of 1,2-dichloroethane were charged therein. Subsequently, while stirring the solution in the flask, 14.3 g (0.106 mol) of trichlorosilane was slowly added dropwise from the dropping funnel under the condition of 25° C. After the completion of dropwise addition, the reaction was carried out by stirring the mixture for 2 hours, and then heating and stirring the mixture at 50° C. for 8 hours. After the reaction, the obtained solid was filtered and purified, to obtain a white solid containing a mixture (cyclic silane dianion salt-containing composition) of dodecachlorodihydrocyclohexasilane dianion salt ($[Ph_4P^+]_2[Si_6H_2Cl_{12}]^{2-}$), tridecachlorohydrocyclohexasilane dianion salt ($[Ph_4P^+]_2[Si_6HCl_{13}]^{2-}$), and tetradecachlorocyclohexasilane dianion salt ($[Ph_4P^+]_2[Si_6Cl_{14}]^{2-}$) at a content of 90% by mass.

Example 3

The inside of a 300-mL four-necked flask equipped with a thermometer, a condenser, a dropping funnel and a stirrer was replaced with nitrogen gas, and thereafter 10.15 g (0.024 mol) of tetraphenylphosphonium bromide, 5.36 g (0.051 mol) of 2,2-dimethoxypropane, 18.97 g (0.147 mol) of diisopropylethylamine and 100 mL of 1,2-dichloroethane were charged therein. Subsequently, while stirring the solution in the flask, 40.0 g (0.295 mol) of trichlorosilane was slowly added dropwise from the dropping funnel under the condition of 25° C. After the completion of dropwise addition, the reaction was carried out by stirring the mixture for 2 hours, and then heating and stirring the mixture at 50° C. for 8 hours. After the reaction, the obtained solid was filtered and purified, to obtain 9.22 g of a white solid containing a mixture (cyclic silane dianion salt-containing composition) of dodecahalodihydrocyclohexasilane dianion salt ($[Ph_4P^+]_2[Si_6H_2X_{12}]^{2-}$) (wherein X is Cl or Br), tridecahalohydrocyclohexasilane dianion salt ($[Ph_4P^+]_2[Si_6HX_{13}]^{2-}$) (wherein X is Cl or Br), and tetradecahalocyclohexasilane dianion salt ($[Ph_4P^+]_2[Si_6X_{14}]^{2-}$) (wherein X is Cl or Br) at a content of 90% by mass.

Example 4

The inside of a 300-mL four-necked flask equipped with a thermometer, a condenser, a dropping funnel and a stirrer was replaced with nitrogen gas, and thereafter 10.11 g (0.024 mol) of tetraphenylphosphonium bromide, 11.13 g (0.027 mol) of 1,3-bis(diphenylphosphino)propane, 18.90 g (0.146 mol) of diisopropylethylamine and 150 mL of 1,2-dichloroethane were charged therein. Subsequently, while stirring the solution in the flask, 40.0 g (0.295 mol) of trichlorosilane was slowly added dropwise from the dropping funnel under the condition of 25° C. After the completion of dropwise addition, the reaction was carried out by stirring the mixture for 2 hours, and then heating and stirring the mixture at 50° C. for 8 hours. After the reaction, the obtained solid was filtered and purified, to obtain 11.81 g of a white solid containing a mixture (cyclic silane dianion salt-containing composition) of dodecahalodihydrocyclohexasilane dianion salt ($[Ph_4P^+]_2[Si_6H_2X_{12}]^{2-}$) (wherein X is Cl or Br), tridecahalohydrocyclohexasilane dianion salt ($[Ph_4P^+]_2[Si_6HX_{13}]^{2-}$) (wherein X is Cl or Br), and tetradecahalocyclohexasilane dianion salt ($[Ph_4P^+]_2[Si_6X_{14}]^{2-}$) (wherein X is Cl or Br) at a content of 90% by mass.

Example 5

The inside of a 300-mL four-necked flask equipped with a thermometer, a condenser, a dropping funnel and a stirrer was replaced with nitrogen gas, and thereafter 10.4 g (0.037 mol) of tetrabutylammonium chloride, 2.90 g (0.032 mol) of 1,2-dimethoxyethane, 12.5 g (0.097 mol) of diisopropylethylamine and 100 mL of 1,2-dichloroethane were charged therein. Subsequently, while stirring the solution in the flask, 25.8 g (0.191 mol) of trichlorosilane was slowly added dropwise from the dropping funnel under the condition of 25° C. After the completion of dropwise addition, the reaction was carried out by stirring the mixture for 2 hours, and then heating and stirring the mixture at 50° C. for 8 hours. After the reaction, the obtained solid was filtered and purified, to obtain a white solid containing a mixture (cyclic silane dianion salt-containing composition) of dodecachlorodihydrocyclohexasilane dianion salt ($[Bu_4N^+]_2[Si_6H_2Cl_{12}]^{2-}$), tridecachlorohydrocyclohexasilane dianion salt ($[Bu_4N^+]_2[Si_6HCl_{13}]^{2-}$), and tetradecachlorocyclohexasilane dianion salt ($[Bu_4N^+]_2[Si_6Cl_{14}]^{2-}$) at a content of 90% by mass.

The invention claimed is:

1. A method for producing a halogenated cyclic silane compound or a salt thereof, which comprises the step of allowing a halosilane compound to react in the presence of both (A) at least one of a phosphonium salt and an ammonium salt, and (B) a compound represented by the following general formula (i):

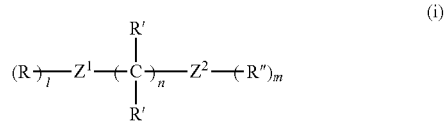

wherein $Z^1$ represents N, O, P or S; $Z^2$ represents O, P or S; R and R" each independently represent an organic group having a carbon number of 1 to 20, which may contain O, P, S or a halogen atom and may have a straight-chain structure, a branched structure, an alicyclic structure or an aromatic ring structure; R' represents a hydrogen atom, or an organic group having a carbon number of 1 to 6, which may have a straight-chain structure, a branched structure or a ring structure; l is 2 when $Z^1$ is N or P, l is 1 when $Z^1$ is O or S, m is 2 when $Z^2$ is P, and m is 1 when $Z^2$ is O or S; n is an integer of 1 to 5; and when R, R' or R" is each plurally present, each may be the same or different, and wherein the halogenated cyclic silane compound or the salt thereof has a silicon-halogen bond, and wherein the compound represented by the general formula (i) contains no tertiary polyamine ligand.

2. The method for producing a halogenated cyclic silane compound or a salt thereof according to claim 1, wherein the reaction is further carried out in the presence of a basic compound.

3. The method for producing a halogenated cyclic silane compound or a salt thereof according to claim 1, wherein the phosphonium salt or the ammonium salt is a quaternary phosphonium salt or a quaternary ammonium salt.

4. The method for producing a halogenated cyclic silane compound or a salt thereof according to claim 1, wherein the phosphonium salt is a salt represented by the following general formula (ii), and the ammonium salt is a salt represented by the following general formula (iii):

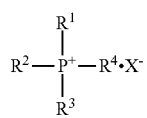

(ii)

wherein $R^1$ to $R^4$ each independently represent a hydrogen atom, an alkyl group or an aryl group;
and $X^-$ represents a monovalent anion;

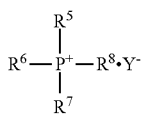

(iii)

wherein $R^5$ to $R^8$ each independently represent a hydrogen atom, an alkyl group or an aryl group;
and $Y^-$ represents a monovalent anion.

5. The method for producing a halogenated cyclic silane compound or a salt thereof according to claim 2, wherein the phosphonium salt or the ammonium salt is a quaternary phosphonium salt or a quaternary ammonium salt.

6. The method for producing a halogenated cyclic silane compound or a salt thereof according to claim 2, wherein the phosphonium salt is a salt represented by the following general formula (ii), and the ammonium salt is a salt represented by the following general formula (iii):

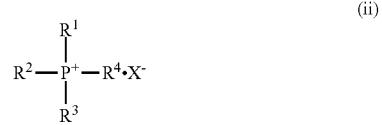

(ii)

wherein $R^1$ to $R^4$ each independently represent a hydrogen atom, an alkyl group or an aryl group;
and $X^-$ represents a monovalent anion;

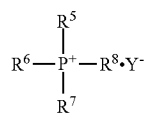

(iii)

wherein $R^5$ to $R^8$ each independently represent a hydrogen atom, an alkyl group or an aryl group;
and $Y^-$ represents a monovalent anion.

7. The method for producing a halogenated cyclic silane compound or a salt thereof according to claim 1, wherein R' represents a hydrogen atom.

8. The method for producing a halogenated cyclic silane compound or a salt thereof according to claim 1, wherein the halogenated cyclic silane compound or the salt thereof is a compound or salt containing a ring formed by continuous six silicon atoms of the halosilane compound.

9. The method for producing a halogenated cyclic silane compound or a salt thereof according to claim 1, wherein the halogenated cyclic silane compound or the salt thereof is represented by general formula (iv):

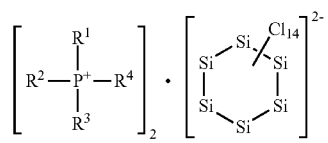

(iv)

wherein $R^1$ to $R^4$ each independently represent a hydrogen atom, an alkyl group or an aryl group.

10. The method for producing a halogenated cyclic silane compound or a salt thereof according to claim 1, wherein the halogenated cyclic silane compound or the salt thereof is represented by general formula (v):

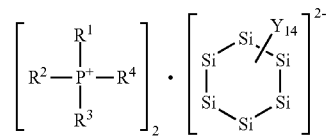

(v)

wherein $R^1$ to $R^4$ each independently represent a hydrogen atom, an alkyl group or an aryl group; and Y represents Cl, Br, or a hydrogen atom.

* * * * *

UNITED STATES PATENT AND TRADEMARK OFFICE
CERTIFICATE OF CORRECTION

PATENT NO. : 9,290,525 B2  
APPLICATION NO. : 13/934577  
DATED : March 22, 2016  
INVENTOR(S) : Abe et al.

Page 1 of 1

It is certified that error appears in the above-identified patent and that said Letters Patent is hereby corrected as shown below:

In the specification

Column 6, line 35-40, Figure (iii), delete "$P^+$" and insert -- $N^+$ --;

Column 13, line 43-47, Figure (iii), delete "$P^+$" and insert -- $N^+$ --; and

Column 14, line 13-18, Figure (iii), delete "$P^+$" and insert -- $N^+$ --.

Signed and Sealed this  
Twenty-seventh Day of September, 2016

Michelle K. Lee  
*Director of the United States Patent and Trademark Office*

UNITED STATES PATENT AND TRADEMARK OFFICE
CERTIFICATE OF CORRECTION

PATENT NO. : 9,290,525 B2  
APPLICATION NO. : 13/934577  
DATED : March 22, 2016  
INVENTOR(S) : Abe et al.

Page 1 of 1

It is certified that error appears in the above-identified patent and that said Letters Patent is hereby corrected as shown below:

In the Specification

Column 6, Line 35-40, Figure (iii), delete "$P^+$" and insert -- $N^+$ --;

Column 13, Line 5, "1 is 2" should read -- l is 2 --;

Column 13, Line 6, "1 is 1" should read -- l is 1 --;

Column 13, Line 43-47, Figure (iii), delete "$P^+$" and insert -- $N^+$ --; and

Column 14, Line 13-18, Figure (iii), delete "$P^+$" and insert -- $N^+$ --.

This certificate supersedes the Certificate of Correction issued September 27, 2016.

Signed and Sealed this  
Twentieth Day of August, 2019

Andrei Iancu  
*Director of the United States Patent and Trademark Office*